US008303503B2

(12) United States Patent
Nair et al.

(10) Patent No.: US 8,303,503 B2
(45) Date of Patent: Nov. 6, 2012

(54) SYSTEM AND METHOD OF CHARACTERIZING VASCULAR TISSUE

(75) Inventors: Anuja Nair, Cleveland Heights, OH (US); D. Geoffrey Vince, Avon Lake, OH (US); Jon D. Klingensmith, Shaker Heights, OH (US); Barry D. Kuban, Avon Lake, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 987 days.

(21) Appl. No.: 11/445,679

(22) Filed: Jun. 1, 2006

(65) Prior Publication Data

US 2006/0241486 A1    Oct. 26, 2006

Related U.S. Application Data

(62) Division of application No. 10/647,971, filed on Aug. 25, 2003, now Pat. No. 7,074,188.

(60) Provisional application No. 60/406,183, filed on Aug. 26, 2002, provisional application No. 60/406,254, filed on Aug. 26, 2002, provisional application No. 60/406,148, filed on Aug. 26, 2002, provisional application No. 60/406,184, filed on Aug. 26, 2002, provisional application No. 60/406,185, filed on Aug. 26, 2002, provisional application No. 60/406,234, filed on Aug. 26, 2002.

(51) Int. Cl.
*A61B 8/00* (2006.01)

(52) U.S. Cl. ........................................ 600/443; 600/437
(58) Field of Classification Search .................. 600/407, 600/437, 443, 459, 462, 466, 467
See application file for complete search history.

(56) References Cited

U.S. PATENT DOCUMENTS 5,417,215 A * 5/1995 Evans et al. .................. 600/442
(Continued)

OTHER PUBLICATIONS

Kerut et al., "Echocardiographic Texture Analysis Using the Wavelet Transform Differentiation of Early Heart Muscle Disease," Ultrasound in Medicine and Biology, 2000, pp. 1445-1453, vol. 26, No. 9, Elsevier, New York, U.S.A.

(Continued)

*Primary Examiner* — Tse Chen
*Assistant Examiner* — Peter Luong
(74) *Attorney, Agent, or Firm* — Haynes and Boone, LLP

(57) ABSTRACT

A system and method is provided for using backscattered data and known parameters to characterize vascular tissue. Specifically, in one embodiment of the present invention, an ultrasonic device is used to acquire RF backscattered data (i.e., IVUS data) from a blood vessel. The IVUS data is then transmitted to a computing device and used to create an IVUS image. The blood vessel is then cross-sectioned and used to identify its tissue type and to create a corresponding image (i.e., histology image). A region of interest (ROI), preferably corresponding to the identified tissue type, is then identified on the histology image. The computing device, or more particularly, a characterization application operating thereon, is then adapted to identify a corresponding region on the IVUS image. To accurately match the ROI, however, it may be necessary to warp or morph the histology image to substantially fit the contour of the IVUS image. After the corresponding region is identified, the IVUS data that corresponds to this region is identified. Signal processing is then performed and at least one parameter is identified. The identified parameter and the tissue type (e.g., characterization data) is stored in a database. In another embodiment of the present invention, the characterization application is adapted to receive IVUS data, determine parameters related thereto (either directly or indirectly), and use the parameters stored in the database to identify a tissue type or a characterization thereof.

20 Claims, 10 Drawing Sheets

U.S. PATENT DOCUMENTS

| | | | |
|---|---|---|---|
| 5,619,998 A | 4/1997 | Abdel-Malek | |
| 6,200,268 B1 * | 3/2001 | Vince et al. | 600/443 |
| 6,264,609 B1 * | 7/2001 | Herrington et al. | 600/443 |
| 6,415,046 B1 * | 7/2002 | Kerut, Sr. | 382/128 |
| 2003/0032880 A1 | 2/2003 | Moore | |

OTHER PUBLICATIONS

Turkoglu et al., "An Expert System for Diagnosis of the Heart Valve Diseases," Expert Systems With Applications, 2002, pp. 229-236, vol. 23, No. 3, Pergamon, Elmsford, U.S.A.

Wear, et al., "Application of Autoregressive Spectral Analysis to Cepstral Estimation of Mean Scattering Spacing," IEEE Transactions on Ultrasonics, Ferroelectrics, and Frequency Control, 1993, pp. 50-58, vol. 40, No. 1, Institute of Electrical and Electronics Engineers, New York, U.S.A.

Zong et al., "Speckle Reduction and Contrast Enhancement of Echocardiograms via Multiscale Nonlinear Processing," IEEE Transactions on Medical Imaging, 1998, pp. 532-540, vol. 17, No. 4, Institute of Electrical and Electronics Engineers, New York, U.S.A.

* cited by examiner

SYSTEM AND METHOD OF CHARACTERIZING VASCULAR TISSUE

CROSS-REFERENCE TO RELATED APPLICATIONS

This is a divisional of U.S. patent application Ser. No. 10/647,971, filed Aug. 25, 2003, now issued as U.S. Pat. No. 7,074,188, which claims the benefit pursuant to 35 U.S.C. § 119(e) of U.S. Provisional Patent Application Nos. 60/406,183, filed Aug. 26, 2002, 60/406,254, filed Aug. 26, 2002, 60/406,148, filed Aug. 26, 2002, 60/406,184, filed Aug. 26, 2002, 60/406,185, filed Aug. 26, 2002, and 60/406,234, filed Aug. 26, 2002, all of which are incorporated herein, in their entirety, by reference.

BACKGROUND OF THE INVENTION

1. Field of the Invention

The present invention relates to vascular tissue, or more particularly, to a system and method of using backscattered data and known parameters to characterize vascular tissue.

2. Description of Related Art

The present invention relates to the intra-vascular ultrasound (IVUS) analysis arts. It finds particular application to a system and method for quantitative component identification within a vascular object including characterization of tissue. It should be appreciated that while the present invention is described in terms of an ultrasonic device, or more particularly the use of IVUS data (or a transformation thereof to characterize a vascular object, the present invention is not so limited. Thus, for example, using backscattered data (or a transformation thereof to characterize any tissue type or composition is within the spirit and scope of the present invention.

Ultrasonic imaging of portions of a patient's body provides a useful tool in various areas of medical practice for determining the best type and course of treatment. Imaging of the coronary vessels of a patient by ultrasonic techniques can provide physicians with valuable information. For example, the image data may show the extent of a stenosis in a patient, reveal progression of disease, help determine whether procedures such as angioplasty or atherectomy are indicated or whether more invasive procedures may be warranted.

In a typical ultrasound imaging system, an ultrasonic transducer is attached to the end of a catheter that is carefully maneuvered through a patient's body to a point of interest such as within a blood vessel. The transducer may be a single-element crystal or probe that is mechanically scanned or rotated back and forth to cover a sector over a selected angular range. Acoustic signals are then transmitted and echoes (or backscatter) from these acoustic signals are received. The backscatter data can be used to identify the type or density of a scanned tissue. As the probe is swept through the sector, many acoustic lines are processed building up a sector-shaped image of the patient. After the data is collected, an image of the blood vessel (i.e., an IVUS image) is reconstructed using well-known techniques. This image is then visually analyzed by a cardiologist to assess the vessel components and plaque content.

Typically, the ultrasonic image data is transferred to a VHS videotape, digitized and then analyzed. This process, however, loses image resolution since the videotape typically has a lower resolution than the originally collected backscatter data. Losing image resolution may result in an inaccurate evaluation of a vessel and its plaque content. Furthermore, certain image characteristics like brightness and contrast will be different for different patients or could vary for the same patient if the cardiologist varies the settings on the IVUS console. The images that are recorded on the videotapes are the same images viewed on the IVUS console screen and, thus, subject to the settings on the console. Since plaque (or tissue type) is identified by its appearance on the screen, errors may occur in the analysis if the screen settings have been modified. Another drawback is that certain information (e.g., tissue composition, etc.) cannot readily be discerned from an IVUS image (at least not to any degree of certainty). Thus, it would be advantageous to have a system and method of characterizing and/or imaging a vascular object that overcomes at least one of these drawbacks.

SUMMARY OF THE INVENTION

The present invention provides a system and method of using backscattered data and known parameters to characterize vascular tissue. Embodiments of the present invention operate in accordance with an ultrasonic device and a computing device comprising a characterization application and a database. Specifically, the ultrasonic device (e.g., intra-vascular ultrasound (IVUS) console and IVUS catheter) is used to acquire RF backscattered data (i.e., IVUS data) from a blood vessel. For example, a transducer may be attached to the end of a catheter and carefully maneuvered through a patient's body to a point of interest. The transducer is then pulsed to acquire echoes or backscattered signals (i.e., IVUS data) reflected from the tissue of the vascular object. The IVUS data is then transmitted to the computing device and used (either by the computing device or the IVUS console) to create an IVUS image.

In a first embodiment of the present invention, the characterization application is adapted to receive and store characterization data (e.g., tissue type data, etc.). Specifically, after the vascular object has been interrogated, the vascular object is cross-sectioned for histology. The cross-section is then prepared with a fixing and staining process that is well known in the art. The staining process allows a clinician to identify a tissue type(s). The identified tissue type (e.g., characterization data) is then provided to the characterization application and stored in the database.

In another embodiment of the present invention, the characterization application is further adapted to create a histology image and identify at least one corresponding region on the IVUS image. In this embodiment, digitized data corresponding to the cross-sectioned vascular object is provided to the characterization application. The digitized data is then used to create a histology image. A region of interest (ROI) on the histology image is then identified by the operator. Preferably, the ROI corresponds to the characterization data, as previously provided. The characterization application is then adapted to identify a corresponding region on the IVUS image. To accurately match the ROI, however, it may be necessary to warp or morph the histology image to substantially fit the contour of the IVUS image. This warping removes histological preparation artifacts caused by cutting the tissue. Accordingly, in one embodiment of the present invention, the characterization application is further adapted to morph the histology image by (i) identifying (or receiving identifying data from an operator on) at least one landmark common to both the histology image and the IVUS image, (ii) use a first algorithm (e.g., a morphometric algorithm) to substantially align the corresponding landmarks, and (iii) use a second algorithm (e.g., a thin plate spline (TPS) deformation technique) to substantially align the non-landmark portions of the object.

In another embodiment of the present invention, the characterization application is further adapted to determine and store parameters associated with the ROI portion of the IVUS image. In this embodiment, the characterization application is adapted to identify the IVUS data that corresponds to the ROI on the IVUS image. After the IVUS data has been identified, and in accordance with one embodiment of the present invention, the characterization application is adapted to identify at least one parameter of the IVUS data. In another embodiment of the present invention, the characterization application is adapted to identify at least one parameter after frequency analysis has been performed (e.g., using fast Fourier transform, the Welch periodogram, autoregressive power spectrum (AR) analysis). The identified parameter is then stored in the database, where it is linked to the characterization data. This data (i.e., stored parameters and characterization data) can then be used to identify or characterize vascular tissue.

In a second embodiment of the present invention, the characterization application is adapted to receive IVUS data, determine parameters related thereto, and use the parameters stored in the database (i.e., histology data) to identify tissue type(s) or characterization(s) thereof. In this embodiment, the characterization application is adapted to receive IVUS data from the IVUS console and identify at least one parameter associated therewith (either directly or indirectly). In other words, the parameters may be identified directly from the IVUS data or from a transformation thereof (e.g., after frequency analysis). The identified parameters are then compared to the parameters stored in the database (i.e., histology data). If a match (either exactly or substantially) is found, the related region is correlated to the tissue type (or characterization) stored in the database. In one embodiment of the present invention, the characterization application is further adapted to display a reconstructed image of the interrogated vascular object, where different tissue types are identified using different colors (e.g., discrete colors, gray-scales, etc.).

A more complete understanding of the system and method of using backscattered data and known parameters to characterize vascular tissue will be afforded to those skilled in the art, as well as a realization of additional advantages and objects thereof, by a consideration of the following detailed description of preferred embodiments. Reference will be made to the appended sheets of drawings which will first be described briefly.

BRIEF DESCRIPTION OF THE DRAWINGS

FIG. 3 illustrates a cross-section of an exemplary vascular object in-vivo and in-vitro.

FIG. 4 illustrates an alternate embodiment of the computing device depicted in FIG. 1.

DETAILED DESCRIPTION OF THE PREFERRED EMBODIMENT

Preferred embodiments of the present invention operate in accordance with an ultrasonic device and a computing device comprising a characterization application and a database. In the detailed description that follows, like element numerals are used to describe like elements illustrated in one or more figures.

Figure 1:
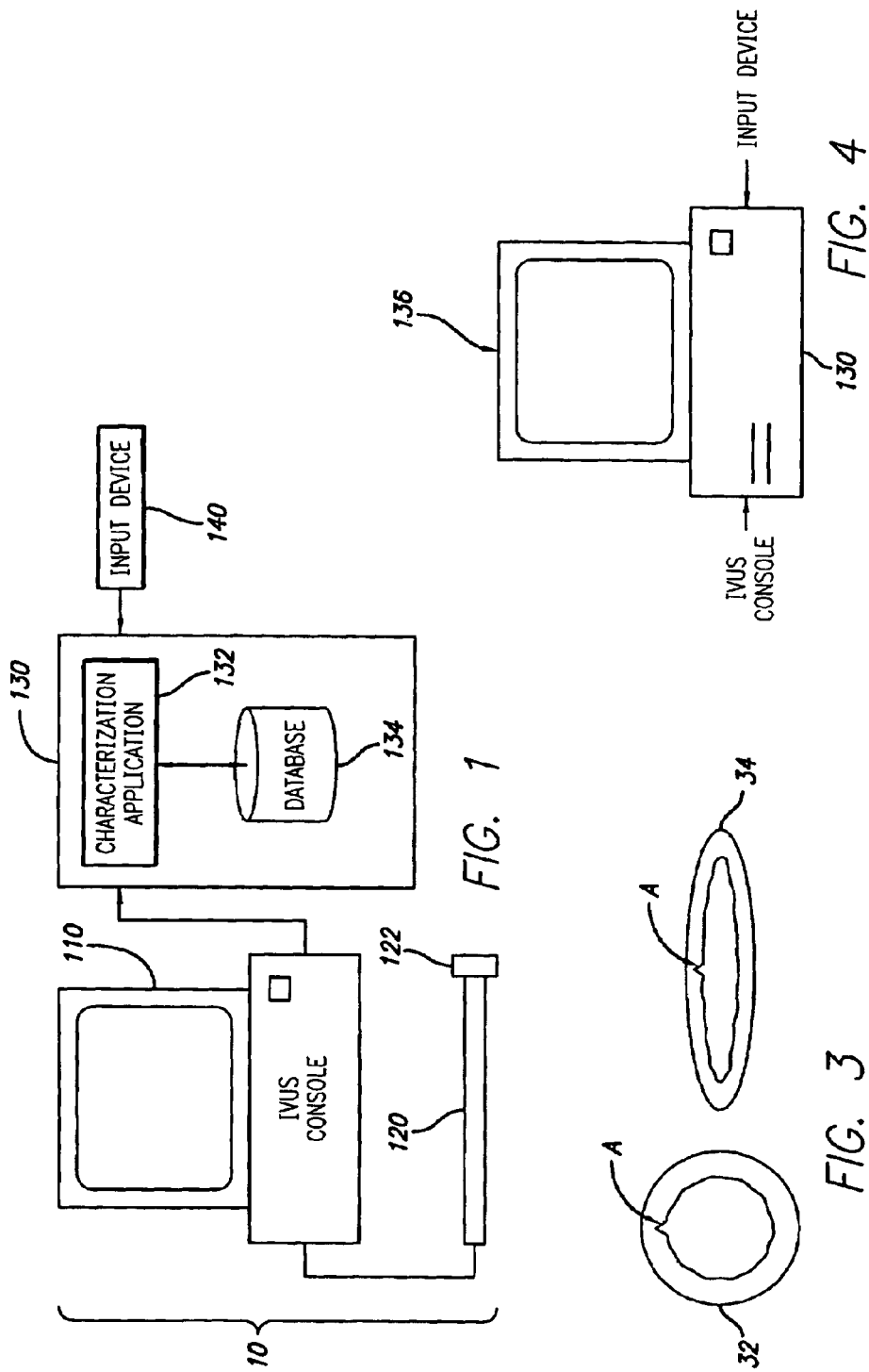
FIG. 1 illustrates a tissue-characterization system in accordance with one embodiment of the present invention, including an IVUS console, an IVUS catheter, a computing device and an input device.
Figure 2:
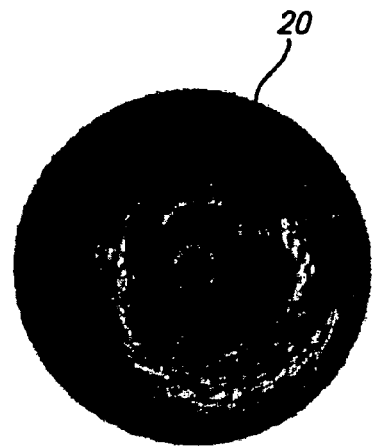
FIG. 2 illustrates an exemplary IVUS image.

FIG. 1 illustrates a tissue-characterization system 10 operating in accordance with a first embodiment of the present invention. In this embodiment, an intra-vascular ultrasound (IVUS) console 110 is electrically connected to an IVUS catheter 120 and used to acquire RF backscattered data (i.e., IVUS data) from a blood vessel. Specifically, a transducer 122 is attached to the end of the catheter 120 and is carefully maneuvered through a patient's body to a point of interest. The transducer is then pulsed to acquire echoes or backscattered signals reflected from the tissue of the vascular object. Because different types and densities of tissue absorb and reflect the ultrasound pulse differently, the reflected data (i.e., IVUS data) can be used to image the vascular object. In other words, the IVUS data can be used (e.g., by the IVUS console 110) to create an IVUS image. An exemplary IVUS image 20 is provided in FIG. 2, where the light and dark regions indicate different tissue types and/or densities. It should be appreciated that the IVUS console 110 depicted herein is not limited to any particular type of IVUS console, and includes all ultrasonic devices known to those skilled in the art (e.g., a C-VIS Clearview Imaging System, etc.). It should further be appreciated that the IVUS catheter 120 depicted herein is not limited to any particular type of catheter, and includes all ultrasonic catheters known to those skilled in the art. Thus, for example, a catheter having a single transducer (e.g., adapted for rotation) or an array of transducers (e.g., circumferentially positioned around the catheter) is within the spirit and scope of the present invention.

Referring back to FIG. 1, the tissue-characterization system 10 further includes a computing device 130 comprising a database 134 and a characterization application 132 electrically connected to the database 134 and adapted to receive IVUS data from the IVUS console 110. It should be appreciated that the database 134 depicted herein includes, but is not limited to, RAM, cache memory, flash memory, magnetic disks, optical disks, removable disks, SCSI disks, IDE hard drives, tape drives and all other types of data storage devices (and combinations thereof, such as RAID devices) generally known to those skilled in the art. It should further be appreciated that the characterization application 132, as depicted and discussed herein, may exist as a single application or as multiple applications, locally and/or remotely stored. It should also be appreciated that the number and location of the components depicted in FIG. 1 are not intended to limit the present invention, and are merely provided to illustrate the environment in which the present invention may operate. Thus, for example, a computing device having a plurality of databases and/or a remotely located characterization application (either in part or in whole) is within the spirit and scope of the present invention.

In one embodiment of the present invention, the characterization application 132 is adapted to receive and store characterization data (e.g., tissue type, etc.). Specifically, after a vascular object has been interrogated (e.g., IVUS data has been collected), a histology correlation is prepared. In other words, the vascular object is dissected or cross-sectioned for histology. In one embodiment of the present invention, the cross-section is previously marked, for example with a suture, so that the histology can be corresponded to a portion of the IVUS image. The cross-section is then prepared with a fixing and staining process that is well known in the art. The staining process allows a clinician to identify a tissue type(s), or a chemical(s) found within (e.g., a chemical corresponding to a particular tissue type, etc.). It should be appreciated that the particular method used to identify or characterize the cross-sectional object is not a limitation of the present invention. Thus, all identification/characterization methods generally known to those skilled in the art are within the spirit and scope of the present invention.

The identified tissue type or characterization (i.e., characterization data) is then provided to the characterization application 132. In one embodiment, as shown in FIG. 1, the characterization data is provided via an input device 140 electrically connected to the computing device 130. The characterization data is then stored in the database 134. It should be appreciated that the input device depicted herein includes, but is not limited to, a keyboard, a mouse, a scanner and all other data-gathering and/or data-entry devices generally known to those skilled in the art. It should further be appreciated that the term tissue type or characterization, as these terms are used herein, include, but are not limited to, fibrous tissues, fibro-lipidic tissues, calcified necrotic tissues, calcific tissues, collagen compositions, cholesterol, thrombus, compositional structures (e.g., the lumen, the vessel wall, the medial-adventitial boundary, etc.) and all other identifiable characteristics generally known to those skilled in the art.

In one embodiment of the present invention, the characterization application is adapted to create a histology image and to identify at least one corresponding region on an IVUS image. Specifically, digitized data is provided to the characterization application (e.g., via the input device 140), where the digitized data corresponds to the cross-sectioned vascular object. The digitized data is then used to create a histology image (i.e., a digital image or outline that substantially corresponds to the vascular object). A region of interest (ROI) on the histology image can then be identified by the operator. Preferably, the ROI is characterized by the characterization data, as previously provided, and may be the entire histology image or a portion thereof. The characterization application is then adapted to identify a corresponding region (e.g., x,y coordinates, etc.) on the IVUS image (i.e., the image created using the raw backscattered data, or the IVUS data).

To accurately match the ROI, however, the histology image may need to be warped to substantially fit the contour of the IVUS image. The warping removes histological preparation artifacts caused by cutting and/or fixing the tissue. For example, as shown in FIG. 3, the shape of a in-vivo vascular object 32 is generally round. Once this object is cut, or cross-sectioned for histology (i.e., creating an in-vitro vascular object 34), the object may appear somewhat distorted, or flattened. Furthermore, the tissue may shrink (e.g., about 30%) when it is put through the fixation process. Thus, in order to identify a corresponding ROI on the IVUS image, the histology image may need to be warped or morphed, to return it to its original shape.

Accordingly, in one embodiment of the present invention, the characterization application is adapted to morph the histology image. Specifically, the characterization application is adapted to identify (or receive identifying data from an operator on) at least one landmark common to both the histology image and the IVUS image (see e.g., FIG. 3, landmark A). The characterization application is then adapted to use (i) a first algorithm (e.g., a morphometric algorithm) to substantially align the corresponding landmarks and (ii) a second algorithm (e.g., a thin plate spline (TPS) deformation technique) to substantially align the non-landmark portions of the object. In other words, the second algorithm is used to shape the regions or boundaries between the landmarks. It should be appreciated that the landmarks discussed herein include, but are not limited to, side branch vessels, identifiable plaque or calcium deposits, and all other vascular tissue landmarks generally known to those skilled in the art.

In one embodiment of the present invention, the characterization application is further adapted to determine and store parameters associated with the ROI portion of the IVUS image. Specifically, the characterization application is adapted to identify the IVUS data (i.e., the raw backscatter data) that corresponds to the ROI identified on the IVUS image. In other words, the IVUS data that was originally used to create the ROI on the IVUS image is identified. In one embodiment of the present invention, the characterization application is further adapted to identify at least one parameter of the identified IVUS data. This parameter is then stored in the database, where it is linked to the characterization data. It should be appreciated, however, that each parameter may be associated with more than one tissue type or characterizations. For example, a first parameter may be common to multiple tissue types, thus requiring additional parameters to narrow the field.

In another embodiment of the present invention, signal analysis (i.e., frequency analysis, etc.) is performed on the identified IVUS data before the parameters are identified. In other words, the IVUS data is converted (or transformed) into the frequency domain (e.g., from the time domain) to identify the frequency spectrum of the ROI. This is because the frequency information obtained from the backscattered signal (or parameters associated therewith) can serve as a "signature" for each tissue type or characteristic. In one embodiment of the present invention, the frequency analysis is performed using a fast Fourier transform (FFT). In another embodiment of the present invention, the frequency analysis is performed using the Welch periodogram. In another embodiment of the present invention, the frequency analysis is performed using autoregressive power spectrum (AR) analysis. At least one parameter of the frequency-based signal is then identified and stored in the database, where it is linked to the characterization data.

In another embodiment of the present invention, both backscattered data (e.g., IVUS data) and its frequency spectrum are analyzed to classify the ROI portion of the IVUS image. Specifically, the frequency spectrum (or more particularly at least one parameter identified therefrom) is used to identify tissue type and the backscattered data is used to identify tissue location. This is because the backscatter data is in the time domain, and can thus be used to spatially identify certain frequencies (or parameters related thereto). For example, if a vascular wall comprises multiple tissue layers, corresponding backscattered data can be used to identify the location of these tissues and the related frequency spectrum can be used to identify tissue types. It should be appreciated that, while certain embodiments have been described in terms of frequency transformation, the present invention is not so limited. Thus, alternate transformations (e.g., wavelet transformation, etc.) are within the spirit and scope of the present invention. It should further be appreciated that the term parameter, as that term is used herein, includes, but is not limited to maximum power, minimum power, frequencies at maximum and/or minimum power, y intercepts (estimated or actual), slope, mid-band fit, integrated backscatter and all parameters generally known to (or discernable by) those skilled in the art. It should also be appreciated that the term "histology data," as that term is used herein, includes data stored in the database (e.g., characterization data, parameters, etc.).

Figure 6:
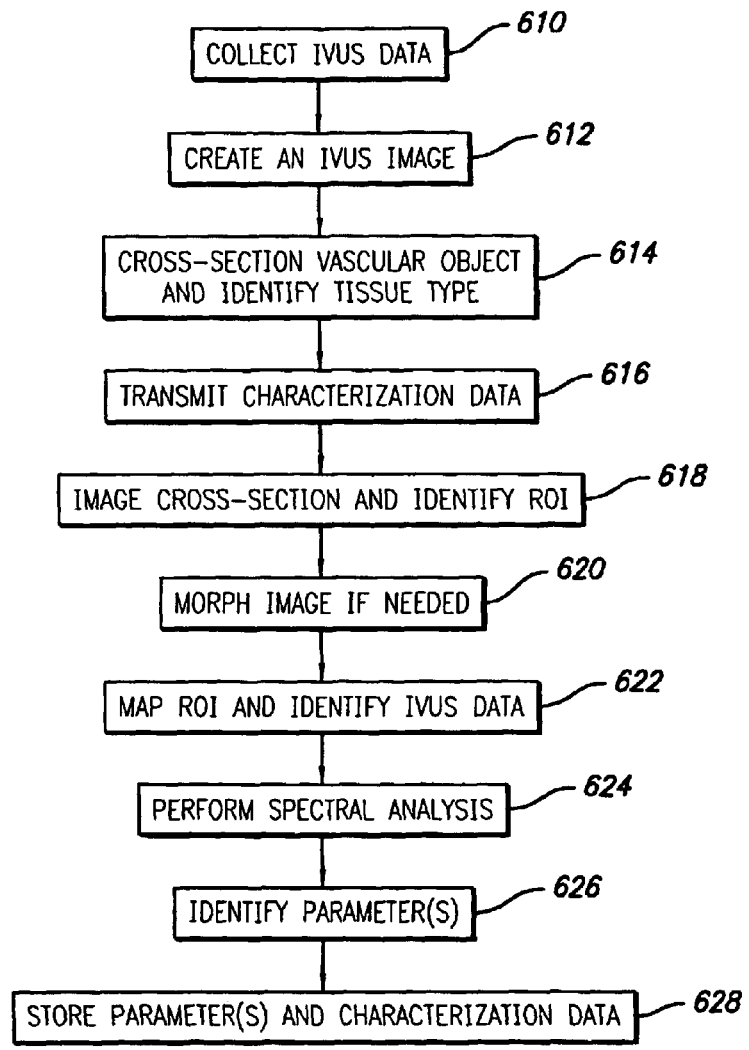
FIG. 6 illustrates a method of characterizing a vascular object in accordance with one embodiment of the present invention.

One method of populating the database is illustrated in FIG. 6. Specifically, at step 610, IVUS data (i.e., RF backscatter data) is collected from a portion of a vascular object. This data is then used to create an IVUS image at step 612. At step 614, the interrogated portion of the vascular object is cross-sectioned and a tissue type (or a characterization thereof is identified. This information (i.e., characterization data) is then transmitted to a computing device (or the equivalent thereof) at step 616. At step 618, an image of the cross-sectioned vascular object is created and a ROI is identified (e.g., by an operator). This image is then morphed, if needed, to substantially match the cross-section image to the IVUS image at step 620. This may include identifying at least one landmark and applying at least one algorithm (e.g., a morphometric algorithm, a TPS deformation technique, etc.). At step 622, the ROI is mapped to the IVUS image and associated IVUS data is identified. Spectral analysis is then performed on the associated IVUS data at step 624, and at least one parameter is identified at step 626. The at least one parameter and the characterization data is then stored at step 628. In one embodiment of the present invention, the at least one parameter is stored such that it is linked to the characterization data. It should be appreciated that the order in which these steps are presented is not intended to limit the present invention. Thus, for example, creating an IVUS image after the vascular object is cross-sectioned is within the spirit and scope of the present invention.

The above-described process is repeated for each tissue component desired to be identified and repeated for each component as many times as desired in order to obtain a more accurate range of signal properties. With the database populated, a tissue type or characteristic can be automatically and accurately identified if the acquired parameters substantially match parameters stored in the database.

Accordingly, in a second embodiment of the present invention, the characterization application is adapted to receive IVUS data, determine parameters related thereto, and use the parameters stored in the database (i.e., histology data) to identify tissue type(s) or characterization(s) thereof. Specifically, with reference to FIG. 1, the characterization application 132 is adapted to receive IVUS data from the IVUS console 110. The characterization application 132 is then adapted to identify at least one parameter associated (either directly or indirectly) with the IVUS data. It should be appreciated that the IVUS data may either be received in real-time (e.g., while the patient is in the operating room) or after a period of delay (e.g., via CD-ROM, etc.). It should further be appreciated that the identified parameters should be related (generally) to the stored parameters. Thus, for example, an estimated Y intercept parameter should be identified if data related to a signal's estimated Y intercept is stored in the database 134 and linked to at least one tissue type. Moreover, if the stored parameters were acquired after frequency analysis was performed (i.e., are related to a frequency-based signal), then frequency analysis (preferably of the same type) should be performed on the IVUS data before parameters are identified. However, the IVUS data may be used to identify spatial information, as previously discussed.

The identified parameters are then compared to the parameters stored in the database (i.e., histology data). If a match (either exactly or substantially) is found, the related region is correlated to the tissue type (or characterization) stored in the database 134 (e.g., as linked to the matching parameters). It should be appreciated that a match may occur as long as the parameters fall within a range of properties for a particular tissue type found in the database.

Figure 5:
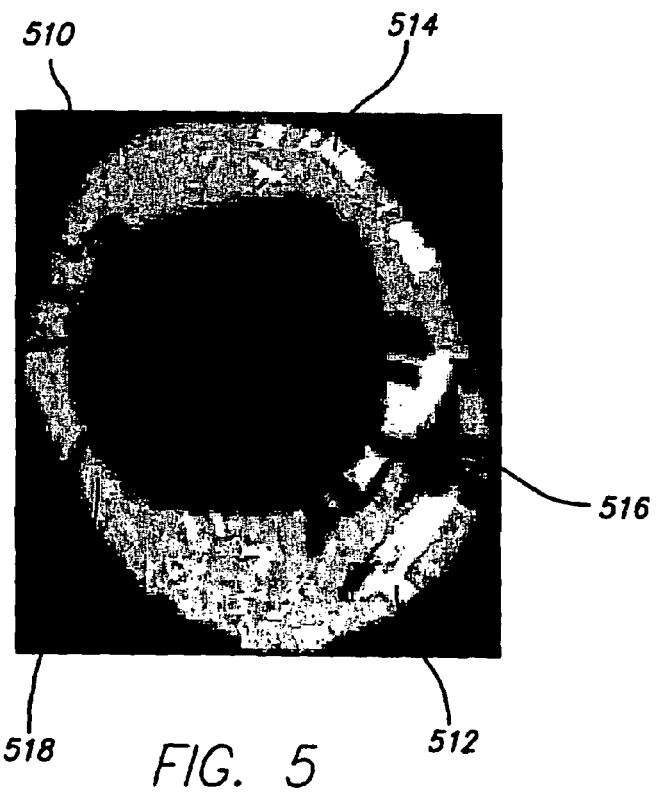
FIG. 5 illustrates an exemplary image of a characterized vascular object.

In one embodiment, after each region is identified, the characterization application is further adapted to display a reconstructed image of the interrogated vascular object on a display. A computing device 130 including such a display 136 is illustrated in FIG. 4. In one embodiment of the present invention, each tissue type (or characterization) is distinguished through the use of gray-scales or discrete colors. For example, FIG. 5 illustrates an exemplary reconstructed vascular object 510, where different tissues (e.g., calcific tissues 512, fibrous tissues 514, calcified necrotic tissues 516 and fibro-lipidic tissues 518) are identified using different shades of gray. Such a system makes different tissue types or characterizations easily identifiable. Additional examples of characterized vascular objects are provided by U.S. Pat. No. 6,200,268, which was issued on Mar. 13, 2001, and is incorporated herein, in its entirety, by reference. It should be appreciated that the reconstructed vascular object may further identify vascular borders. Systems and methods of identifying vascular borders are provided by U.S. Provisional Application Nos., 60/406,184, 60/406,234, and 60/406,185, which were filed Aug. 26, 2002, and by U.S. Pat. No. 6,381,350, which issued Apr. 30, 2002, and are incorporated herein, in their entirety, by reference.

EXAMPLE

Data were acquired from fifty-one human left anterior descending (LAD) coronary arteries obtained at autopsy, with IRB approval from the Cleveland Clinic Foundation. The subjects were 39 males and 12 females (18 black, 33 white). Mean ages were 56±12 years. The study sample was limited to those without prior cardiac percutaneous interventions or surgical revascularizations.

Tissue Preparation

Figure 7:
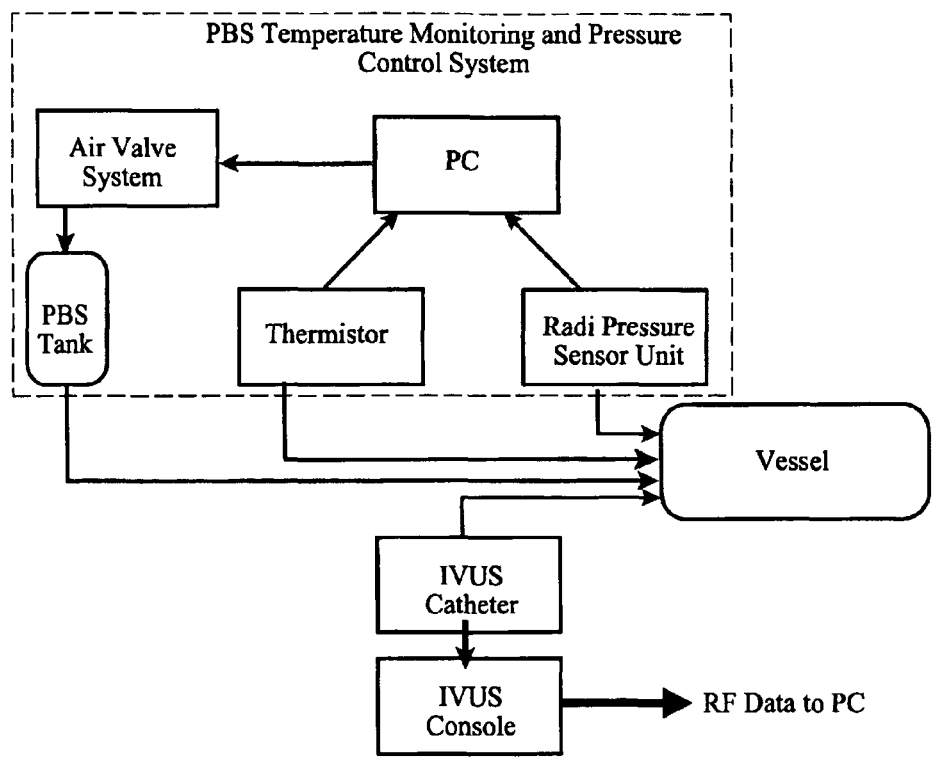
FIG. 7 illustrates an experimental setup utilized to evaluate a plurality of left anterior descending coronary arteries according to an embodiment of the present disclosure.

The arteries were excised from the ostium to apex including approximately 40 mm of surrounding fat and muscle tissue to maintain vessel support and mounted in a dissecting tray approximating their orientation in situ. A computer controlled air valve system was used to maintain flow of phosphate buffered saline through the vessels. Side-branches were clamped to preserve the perfusion pressure of 100 mmHg. A RADI wire (RADI Medical Systems, Reading, MA) was used to monitor pressure. FIG. 7 displays the experimental setup and conditions used while imaging the LADs. This setup has been tested and employed by our group in previous studies. (Nair A, Kuban B D, Obuchowski N. et al. Assessing spectral algorithms to predict atherosclerotic plaque composition with normalized and raw intravascular ultrasound data. *Ultrasound in Medicine & Biology.* 2001;27:1319-1331 and Vince D G, Dixon K J, Cathren R M, et al. Comparison of texture analysis methods for the characterization of coronary plaques in intravascular ultrasound images. *Computerized Medical Imaging and Graphics.* 2000;24:221-229.)

Data Acquisition: IVUS and Histology

IVUS data were acquired using a Hewlett-Packard SONOS clinical IVUS console (Hewlett-Packard Co., Andover, Ma.) and 30 MHz, 2.9 F, mechanically rotating IVUS catheters (Boston Scientific Corp., Watertown, Ma.). After interrogating each vessel with an IVUS catheter, sections with substantial plaque (on average 2 regions per vessel) were identified for data acquisition via manual pullback. Cross-sectional area stenosis greater than 30-40%, as determined by IVUS, was considered significant for the study. RF data was digitized and stored in a Pentium PC for offline analysis. The imaged plaque sites (n=88) were then marked with sutures for collecting the corresponding matched histology.

Each vessel was pressure perfused with Histochoice™ fixative (Amresco, Solon, Oh.) at 100 mmHg to maintain its orientation and size for comparison with the IVUS images. Tissue was processed according to standard laboratory procedures. Two 4 μm sections were collected from each tissue block (at the suture site) and stained with hematoxylin and eosin, and with Movat pentachrome stains.

Histology Analysis

Histology sections were digitized and analyzed by one of the authors, who was blinded to the IVUS data acquisition. Four plaque types (collagen, fibro-lipid, calcium, and calcified-necrosis) were defined. (Nair A, Kuban B D, Obuchowski N. et al. Assessing spectral algorithms to predict atherosclerotic plaque composition with normalized and raw intravascular ultrasound data. *Ultrasound in Medicine & Biology.* 2001;27:1319-1331.) Areas of densely packed collagen were termed fibrous and those with significant lipid interspersed in collagen were labeled fibro-lipidic. Necrotic regions comprising cholesterol clefts, foam cells, and micro-calcifications were termed calcified-necrosis. Finally, calcium deposits without adjacent necrosis were identified as calcium. The Movat stain sections were used as the gold-standard for validations.

IVUS-Histology Correlation

Figure 8:
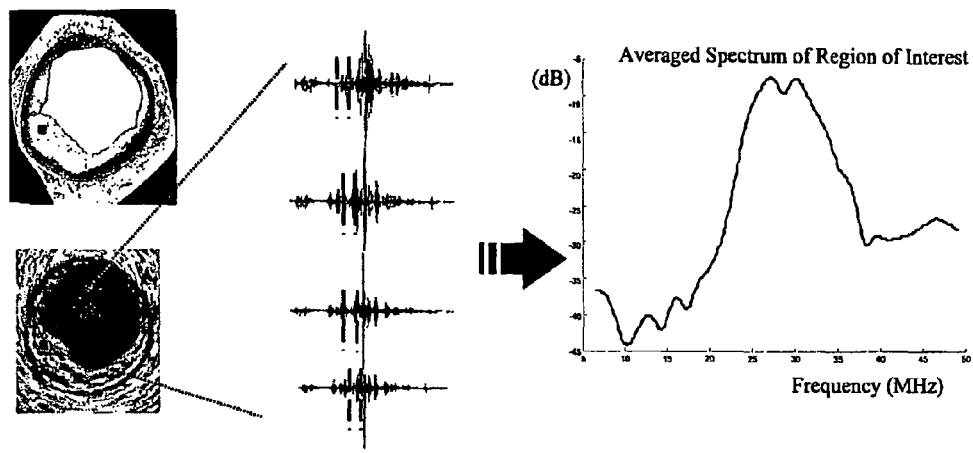
FIG. 8 illustrates imaging data for a region of interest of a vessel in several formats according to an embodiment of the present disclosure.

IVUS B-mode images were reconstructed from the RF data via custom software (IVUSLab) written by our group. (Klingensmith J, Vince D., Kuban B, et al. Assessment of coronary compensatory enlargement by three-dimensional intravascular ultrasound. *International Journal of Cardiac Imaging.* 2000;16:87-98.) Software was also developed to maintain the 1:1 correspondence between the reconstructed IVUS and digitized histology images, which is essential for accurate selection of the regions of interest (ROI). The histology images were first registered, scaled and warped by mathematical techniques (Nair A, Kuban B D, Obuchowski N. et al. Assessing spectral algorithms to predict atherosclerotic plaque composition with normalized and raw intravascular ultrasound data. *Ultrasound in Medicine & Biology.* 2001;27: 1319-1331) to fit the corresponding IVUS reconstructed image. The Movat images were employed to identify homogenous ROIs representing the four plaque components, and the corresponding regions were highlighted on the IVUS images in software. This allowed identification of the backscattered ultrasound signal data representative of the ROIs. FIG. 8 provides a schematic of this procedure. Each ROI was 64 backscattered RF data samples in length (approximately 480 μm), and 12±4 scan lines in width (240 scan lines form one IVUS image with the HP SONOS console).

IVUS Data Analysis

Figure 9:
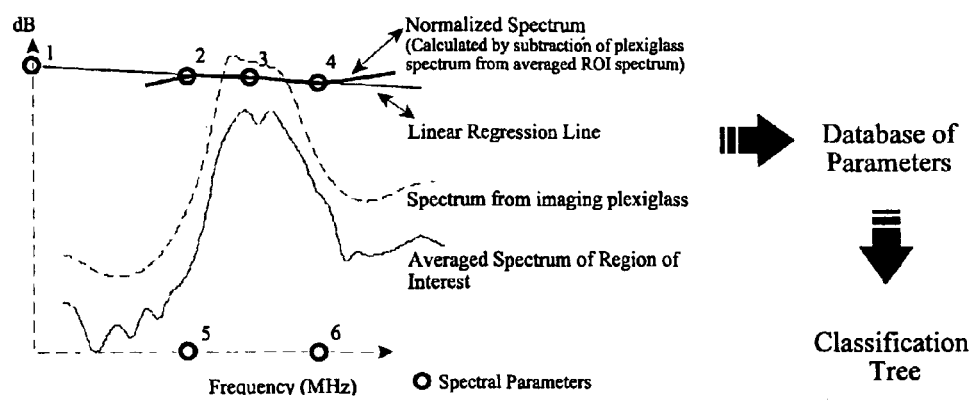
FIG. 9 illustrates parameter computation from normalized spectra according to an embodiment of the present disclosure.

IVUS RF signal data for the ROIs identified from histology were processed in MATLAB® (The MathWorks Inc., Natick, Ma.) by previously developed routines (Nair A, Kuban B D, Obuchowski N. et al. Assessing spectral algorithms to predict atherosclerotic plaque composition with normalized and raw intravascular ultrasound data. *Ultrasound in Medicine & Biology.* 2001;27:1319-1331) such that the frequency spectrum is calculated by a mathematical autoregressive (AR) model for each line in an ROI and then averaged over the width of the ROI. AR processes are known to be more appropriate for short data records, like IVUS signals, than discrete Fourier transforms and have been shown to result in high resolution of spectral estimates. (Baldeweck T, Laugier P, Herment A, et al. Application of autoregressive spectral analysis for ultrasound attenuation estimation: Interest in highly attenuating medium. *IEEE Transactions on Ultrasonics, Ferreolectrics, and Frequency Control.* 1995;42:99-110.) Preliminary work in this study estimated the optimum AR model order (order 10) for characterizing plaque components, after testing several models. Further, the optimized AR spectra was normalized and then used to compute eight spectral parameters (maximum power, corresponding frequency, minimum power, corresponding frequency, slope, y-intercept, mid-band fit and integrated backscatter) for each ROI. FIG. 9 describes parameter computation from normalized spectra. The more commonly used windowed fast Fourier transform (WFT) algorithm (Nair A, Kuban B D, Obuchowski N. et al. Assessing spectral algorithms to predict atherosclerotic plaque composition with normalized and raw intravascular ultrasound data. *Ultrasound in Medicine & Biology.* 2001;27:1319-1331 and Moore M P, Spencer T, Salter D M, et al. Characterization of coronary atherosclerotic morphology by spectral analysis of radiofrequencey signal: In vitro intravascular ultrasound study with histological and radiological validation. *Heart.* 1998;79:459-467 and Watson R J, McLean C C, Moore M P, et al. Classification of arterial plaque by spectral analysis of in vitro radio frequency intravascular ultrasound data. *Ultrasound in Medicine & Biology.* 2000;26:73-80) was also applied to calculate spectra and compared to the AR technique.

Statistical Classification

Seventy-five percent of the data (training set for model-building) representing each plaque component were randomly selected for computing classification trees with the statistics software S-Plus (Statistical Sciences, Inc., Seattle, Wa.). Classification tree modeling is an exploratory technique for discovering structure in data and can be used to devise prediction rules from multivariate data. (Brieman L, Friedman J H, Olshen R A, et al., Classification and regression trees. Chapman and Hall/CRC, New York, NY, 1993.) Such classification schemes comprise a collection of guidelines that are determined by a procedure called recursive partitioning. At each juncture in a tree, unclassified data are separated based on one variable (spectral parameter) that displays maximum separation of the plaque types. Previous work has proven the advantage of these trees in plaque classification as opposed to studying separation of data by one-way analysis of variance. (Nair A, Kuban B D, Obuchowski N. et al. Assessing spectral algorithms to predict atherosclerotic plaque composition with normalized and raw intravascular ultrasound data. *Ultrasound in Medicine & Biology.* 2001;27:1319-1331.) In addition, classification trees account for non-additive behavior in data, because they consider inter-variable interactions that might be unknown, and would be overlooked with linear regression techniques. In the context of plaque components, these interactions could include presence of micro-calcifications in necrotic areas, even though necrosis could be present in absence of calcifications.

The trees were programmed in MATLAB® and used to resolve the type of plaque in the remaining 25% of the test data. The results were validated with the corresponding histology to determine predictive accuracy, sensitivity and specificity from widely accepted equations in bio-medical literature. (Metz CE. Basic principles of roc analysis. *Seminars in Nuclear Medicine.* 1978;VIII:283-298.) Two classification trees were computed, one for the spectral parameters from the WFT and the other for parameters from the mathematical AR spectra.

Automated Plaque Characterization

Figure 10:
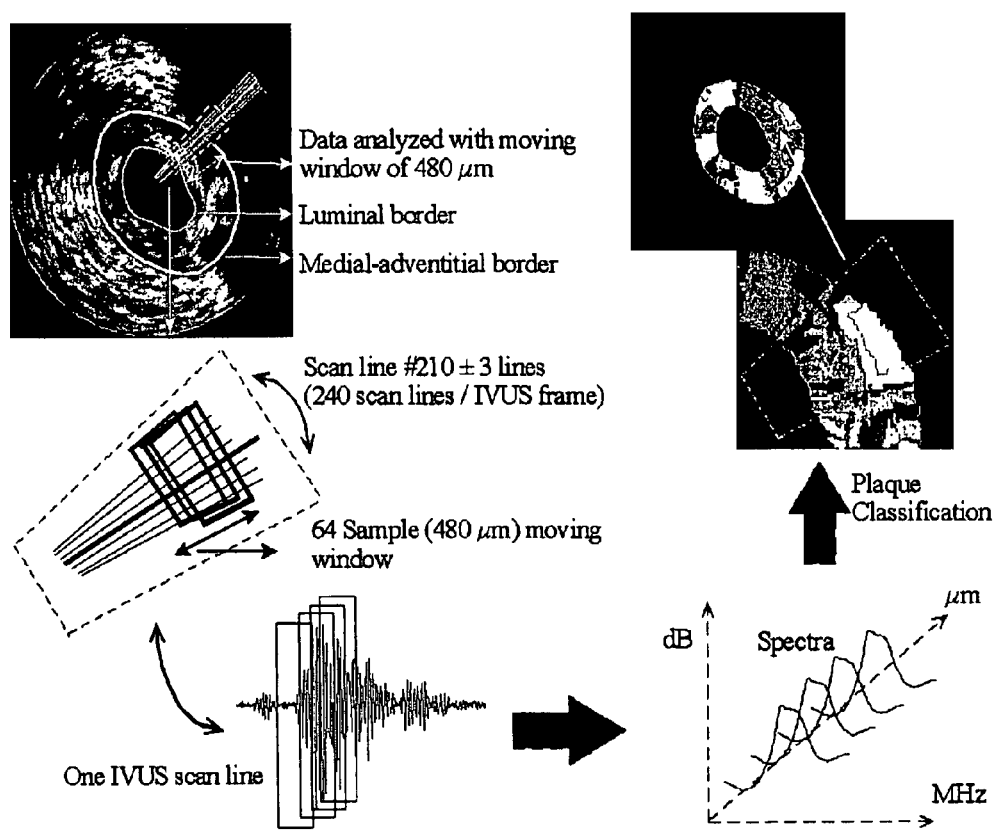
FIG. 10 illustrates a technique for generating plaque tissue characterization maps according to an embodiment of the present disclosure.

The classification schemes were built such that they could decipher plaque components in user defined ROIs. While this is useful, it requires user intervention to identify specific regions that should be classified. Therefore, the next goal in the study was to use these classification schemes to generate tissue maps of entire plaque cross-sections. IVUS data from 3 complete vessel sections were analyzed in MATLAB® to reconstruct tissue maps with the most accurate classification tree. The cases analyzed were not part of the training data that were employed to compute the trees. FIG. 10 illustrates the technique employed. First, IVUSLab software (Klingensmith J., Vince D, Kuban B, et al. Assessment of coronary compensatory enlargement by three-dimensional intravascular ultrasound. *International Journal of Cardiac Imaging.* 2000;16: 87-98) was utilized to outline the plaque luminal and medial-adventitial borders. The IVUS data samples representing only the plaque area, delineated by the outlines, were identified and isolated. Secondly, each scan line was analyzed separately using a moving window 480 μm in length. Frequency spectra were calculated of samples within the window, and spectral parameters were derived (see FIG. 9). The classification tree determined the plaque component type using these parameters, and a plaque type was assigned to the center sample in the window. The window was then moved by one sample and data were re-analyzed. Hence, each sample was given a particular value corresponding to a plaque component.

The plaque component values were assigned color codes and the tissue maps were reconstructed in IVUSLab software. Conforming with the typical Movat stains, fibrous regions were marked in yellow. Fibro-lipidic, calcified, and calcified-necrosis were labeled green, purple and red, respectively. These tissue maps were then visually compared to the Movat stain histology sections to assess the accuracy of the plaque characterization.

Results

Eighty eight plaque sections of interest were identified for data acquisition from the 51 vessels. ROIs were selected from histology sections for fibrous (n=101), fibro-lipidic (n=56), calcified (n=50) and calcified-necrotic (n=70) areas.

Statistical Classification with Frequency Spectra

Classification trees were computed for the AR and the WFT spectra with 75% of the ROIs (n=208) for each plaque component, and then evaluated with the remaining 25% of test data (n=69). The predictive accuracy, sensitivity, and specificity for the training and test data sets for the AR and the WFT spectral trees are displayed in FIGS. 11 and 12 respectively. Both trees performed well, although the AR technique surpassed the WFT in the overall classification.

Figure 11:
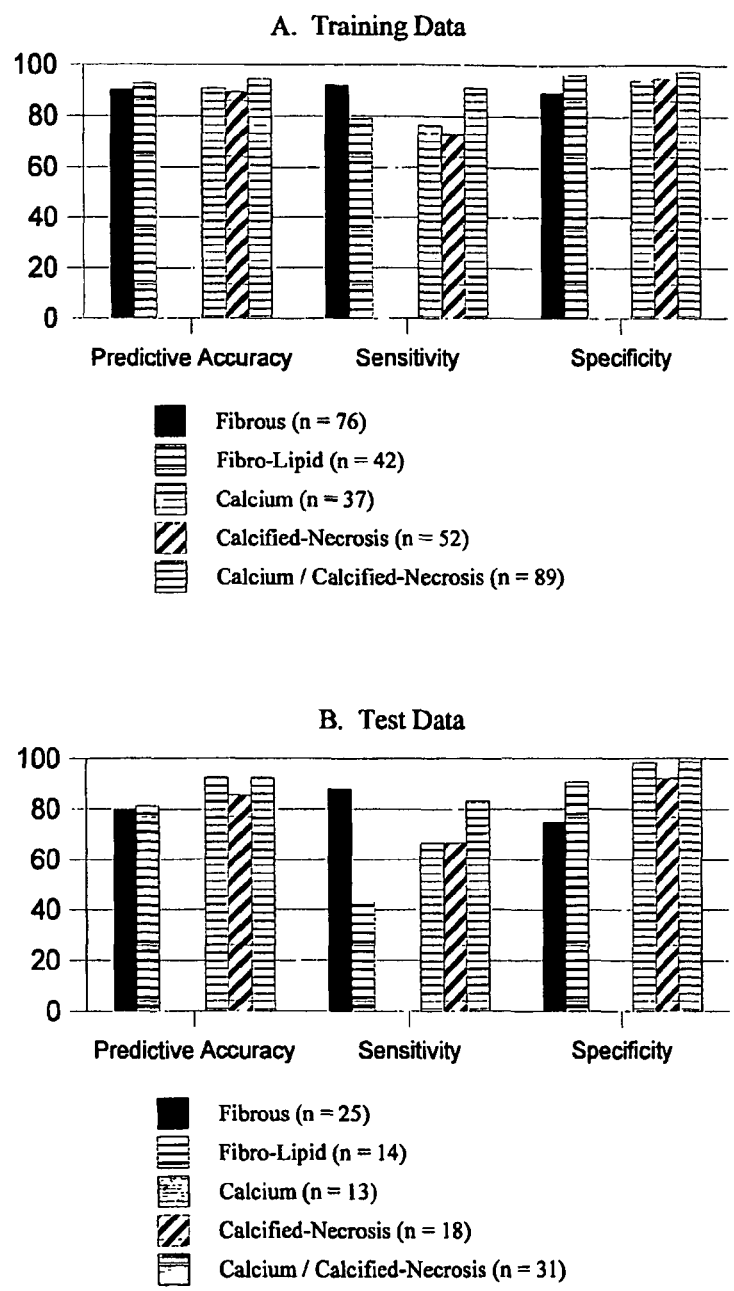
FIG. 11 illustrates predictive accuracy, sensitivity, and specificity for training and test data using an autoregressive model according to an embodiment of the present disclosure.
Figure 12:
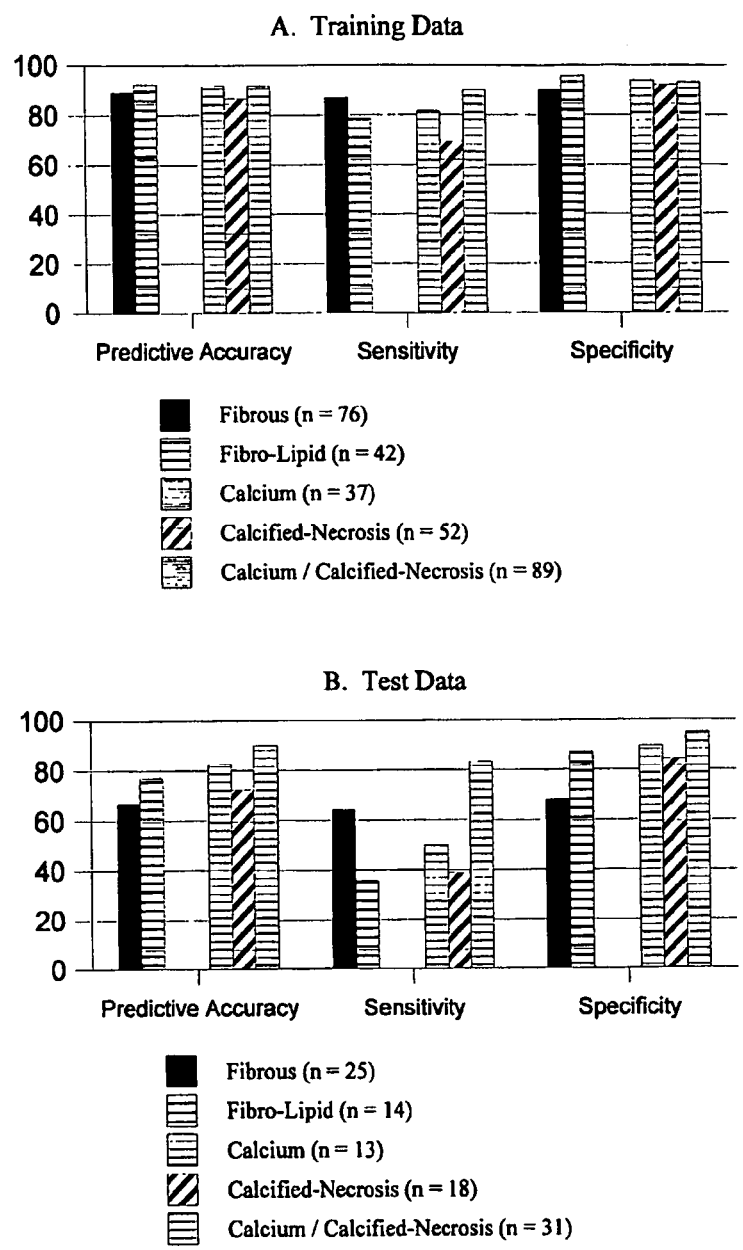
FIG. 12 illustrates predictive accuracy, sensitivity, and specificity for training and test data using a windowed fast Fourier transform algorithm according to an embodiment of the present disclosure.

The AR tree classified fibrous, fibro-lipidic, calcified and calcified-necrotic regions with high predictive accuracies of 90.4%, 92.8%, 90.9% and 89.5%, respectively for the training data and 79.7%, 81.2%, 92.8% and 85.5%, respectively for the test data. The corresponding results for the WFT tree were 88.9%, 92.3%, 91.8%, and 86.5% for training and 66.7%, 76.8%, 82.6% and 72.5% for test data. This trend was also observed in the sensitivities and specificities (FIGS. 11 and 12) for characterizing the plaque components. All calcified regions were then combined as one plaque type (n=120) and the classification trees were reassessed (FIGS. 11 and 12). This increased the accuracies for AR and WFT to 94.7% and 91.8%, respectively for training data, and 92.8% and 89.9% for test data.

Automated Plaque Characterization: Tissue Map Reconstruction

Figure 13:
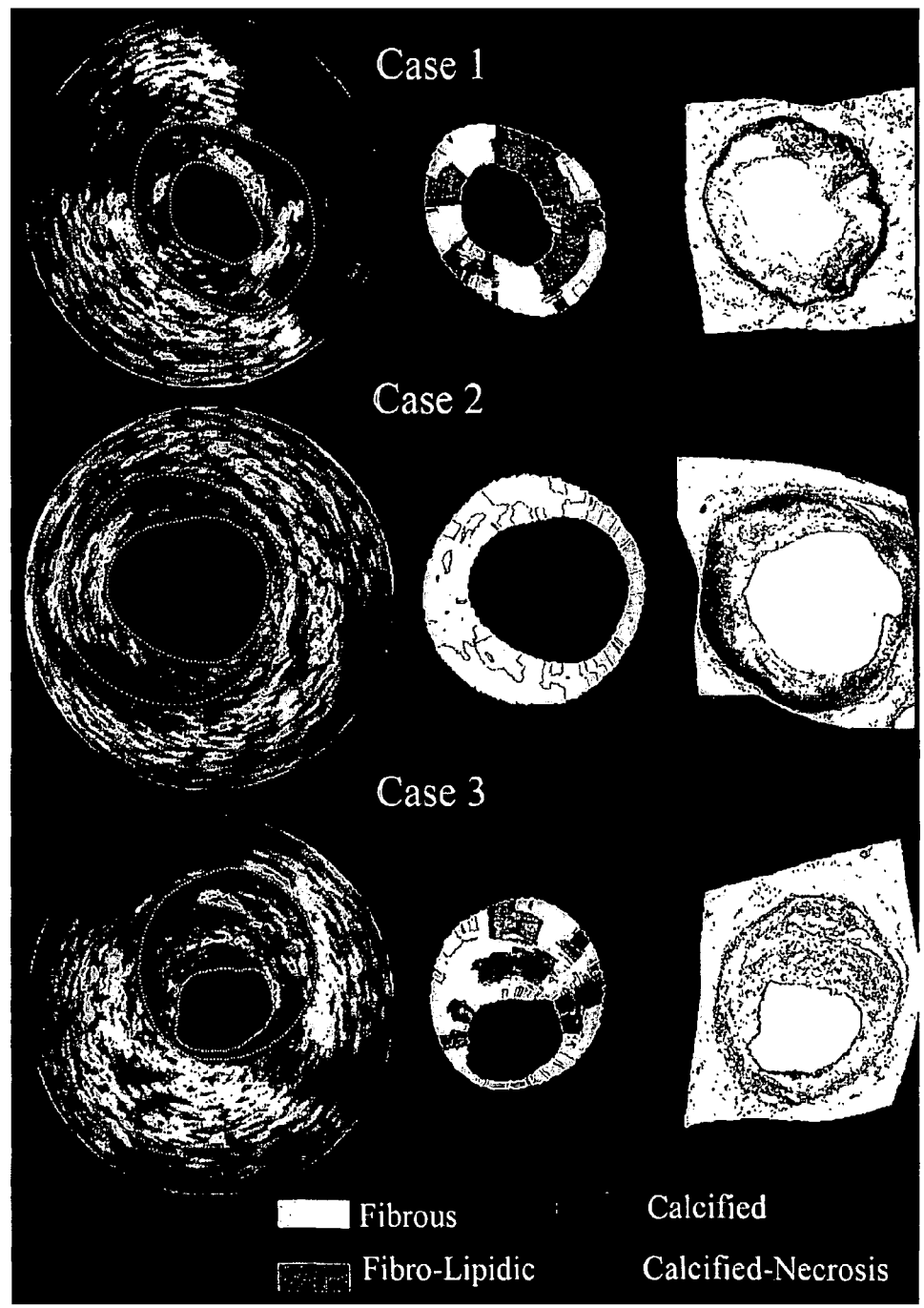
FIG. 13 illustrates a color-coded tissue map according to an embodiment of the present disclosure.

The AR classification scheme was used to assess the plaque composition of three random representative complete vessel sections that were not used as part of the training data. The predicted pathology was displayed as color-coded tissue maps (FIG. 13) and was compared to the corresponding Movat stain sections, as the gold-standard. There was good visual correlation between histology and the RF reconstructed tissue maps. In contrast to the standard IVUS display, these tissue maps could differentiate areas of micro-calcifications (Case #1: 9 o'clock; Case #3: 12 o'clock), heavy calcification (Case #1: 12-2 o'clock and 4-5 o'clock), mixed fibro-lipidic (Case #2, green areas on tissue map corresponding to the lighter areas in the Movat stain), and areas of necrosis adjacent to calcification (Case #3: 12 o'clock, region below calcification separated by collagen).

Having thus described embodiments of a system and method of using backscattered data and known parameters to characterize a vascular tissue, it should be apparent to those skilled in the art that certain advantages of the system have been achieved. It should also be appreciated that various modifications, adaptations, and alternative embodiments thereof may be made within the scope and spirit of the present invention. The invention is further defined by the following claims.

What is claimed is:

1. A method, performed by a computer system comprising a non-transitory computer-readable medium storing computer-executable instructions of a characterization application, for characterizing a vascular object, comprising the steps, facilitated by the computer system executing the computer-executable instructions of the characterization application, of:

utilizing an ultrasound device to acquire ultrasound data from a portion of a vascular object;

constructing an intravascular ultrasound (IVUS) image of the portion of the vascular object using the ultrasound data;

obtaining histology data from a histology performed on the portion of the vascular object;

constructing a histology image of the portion of the vascular object using the histology data;

identifying at least one landmark common to the IVUS image and the histology image;

applying a morphometric algorithm to the first and second images to substantially align the at least one landmark common to the IVUS image and the histology image; and applying a second algorithm to the IVUS image and the histology image to substantially align the non-landmark portions of the IVUS and histology images.

2. The method of claim 1, further comprising:

identifying a first region of interest of the histology image having a first tissue type;

identifying a first portion of the IVUS image corresponding to the first region of interest of the histology image;

identifying a first portion of the ultrasound data corresponding to the first portion of the IVUS image corresponding to the first region of interest of the histology image;

associating one or more parameters of the first portion of the ultrasound data with the first tissue type.

3. The method of claim 2, further comprising:

identifying a second region of interest of the histology image having a second tissue type, the second tissue type being different than the first tissue type;

identifying a second portion of the IVUS image corresponding to the second region of interest of the histology image;

identifying a second portion of the ultrasound data corresponding to the second portion of the IVUS image corresponding to the second region of interest of the histology image; and associating one or more parameters of the second portion of the ultrasound data with the second tissue type.

4. The method of claim 3, further comprising storing in memory the one or more parameters associated with the first tissue type and the one or more parameters associated with the second tissue type.

5. The method of claim 2, further comprising performing a frequency transformation on the first portion of the ultrasound data.

6. The method of claim 5, wherein the one or more parameters associated with the first tissue type are identified after performing the frequency transformation.

7. The method of claim 6, wherein the frequency transformation comprises using a fast Fourier transform (FFT).

8. The method of claim 6, wherein the frequency transformation comprises using a Welch periodogram.

9. The method of claim 6, wherein the frequency transformation comprises using an autoregressive power spectrum (AR) analysis.

10. The method of claim 2, further comprising performing a wavelet transformation on the first portion of the ultrasound data.

11. The method of claim 10, wherein the one or more parameters associated with the first tissue type are identified after performing the wavelet transformation.

12. The method of claim 2, wherein the first tissue type is selected from the group of tissues consisting of fibrous tissues, fibro-lipidic tissues, calcified necrotic tissues, and calcific tissues.

13. The method of claim 2, wherein the one or more parameters associated with the first tissue are selected from the group of parameters consisting of maximum power, minimum power, frequency at maximum power, frequency at minimum power, y intercept, slope, mid-band fit, and integrated backscatter.

14. The method of claim 1, wherein the second algorithm is a thin plate spline deformation technique.

15. A method, comprising:

utilizing an imaging device to obtain imaging data of a vascular object;

constructing a first image of the vascular object using the imaging data, the first image being an intravascular ultrasound (IVUS) image;

obtaining histology data from a histology performed on the vascular object;

constructing a second image of the vascular object using the histology data;

identifying a first region of interest of the second image, the first region of interest corresponding to a portion of vascular object having a first tissue type;

identifying at least one landmark common to the first and second images;

applying a first algorithm to the first and second images to substantially align the at least one landmark common to the first and second images;

applying a second algorithm to the first and second images to substantially align the non- landmark portions of the first and second images;

after aligning the first and second images using the first and second algorithms, identifying a first portion of the first image corresponding to the first region of interest of the second image;

identifying a first portion of the imaging data corresponding to the first portion of the first image corresponding to the first region of interest of the second image; and associating one or more parameters of the first portion of the imaging data with the first tissue type.

16. The method of claim 15, further comprising:

identifying a second region of interest of the second image, the second region of interest corresponding to a portion of vascular object having a second tissue type;

after aligning the first and second images using the first and second algorithms, identifying a second portion of the first image corresponding to the second region of interest of the second image;

identifying a second portion of the imaging data corresponding to the second portion of the first image corresponding to the second region of interest of the second image; and associating one or more parameters of the second portion of the imaging data with the second tissue type.

17. The method of claim 16, further comprising:

storing in memory the one or more parameters associated with the first tissue type and the one or more parameters associated with the second tissue type.

18. The method of claim 17, further comprising:

obtaining imaging data of a second vascular object;

comparing parameters of the imaging data of the second vascular object to the one or more parameters associated with the first and second tissue types stored in memory; and characterizing a tissue type for one or more portions of the second vascular object based on the comparison of the parameters of the imaging data of the second vascular object to the one or more parameters associated with the first and second tissue types stored in memory.

19. A method of characterizing vascular tissue, the method comprising:

providing a data storage device having stored thereon a plurality of tissue types and associated parameters, each of the plurality of tissue types being associated with one or more parameters, wherein for each of the plurality of tissue types the one or more parameters associated with that tissue type is determined by:

obtaining ultrasound data of a sample vascular object;

constructing a first image of the sample vascular object using the ultrasound data, the first image being an intravascular ultrasound (IVUS) image;

obtaining histology data from a histology performed on the sample vascular object;

constructing a second image of the sample vascular object using the histology data;

identifying a region of interest of the second image, the region of interest corresponding to a portion of sample vascular object having a tissue type;

identifying at least one landmark common to the first and second images;

applying a first algorithm to the first and second images to substantially align the at least one landmark common to the first and second images;

applying a second algorithm to the first and second images to substantially align the non-landmark portions of the first and second images;

after aligning the first and second images using the first and second algorithms, identifying a portion of the first image corresponding to the region of interest of the second image;

identifying a portion of the ultrasound data corresponding to the portion of the first image corresponding to the region of interest of the second image; and determining one or more parameters of the portion of the ultrasound data associated with the tissue type;

obtaining ultrasound data of a vascular object;

comparing parameters of the ultrasound data of the vascular object to the one or more parameters associated with the plurality of tissue types stored in data storage device; and characterizing a tissue type for one or more portions of the vascular object based on the comparison of the parameters of the ultrasound data of the vascular object to the one or more parameters associated with each of the plurality of tissue types stored on the data storage device.

20. The method of claim 19, wherein the first algorithm is a morphometric algorithm and the second algorithm is a thin plate spline deformation technique.

* * * * *